United States Patent
Ibrahim et al.

(10) Patent No.: US 9,939,409 B2
(45) Date of Patent: Apr. 10, 2018

(54) SYSTEMS AND METHODS FOR INTEGRATING ION MOBILITY AND ION TRAP MASS SPECTROMETERS

(71) Applicant: Battelle Memorial Institute, Richland, WA (US)

(72) Inventors: Yehia M. Ibrahim, Richland, WA (US); Sandilya Garimella, Richland, WA (US); Spencer A. Prost, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/227,743

(22) Filed: Aug. 3, 2016

(65) Prior Publication Data

US 2018/0038831 A1 Feb. 8, 2018

(51) Int. Cl.
*H01J 49/00* (2006.01)
*G01N 27/00* (2006.01)
*G01N 27/62* (2006.01)
*H01J 49/42* (2006.01)

(52) U.S. Cl.
CPC ........ *G01N 27/622* (2013.01); *H01J 49/0031* (2013.01); *H01J 49/425* (2013.01)

(58) Field of Classification Search
CPC .... H01J 49/0031; H01J 49/061; H01J 49/425; G01N 27/622
USPC ............................. 250/281, 282, 286, 288
See application file for complete search history.

(56) References Cited

U.S. PATENT DOCUMENTS

| 7,560,688 | B2 | 7/2009 | Clowers et al. | |
| 9,269,548 | B2 | 2/2016 | Belov | |
| 2012/0261564 | A1* | 10/2012 | Belov | H01J 49/0031 250/282 |
| 2013/0161506 | A1 | 6/2013 | Ugarov | |
| 2014/0025314 | A1 | 1/2014 | Crowell et al. | |
| 2015/0364305 | A1 | 12/2015 | Wang, Jr. | |

OTHER PUBLICATIONS

Mikhail Belov et al., *Interfacing Ion Mobility with Orbitrap: Novel Hyphenated Approach to Biochemical Analysis*, Pacific Northwest National Laboratory (2011).
Mikhail E. Belov et al., *Multiplexed Ion Mobility Spectrometry-Orthogonal Time-of-Flight Mass Spectometry*, Analytical Chemistry, vol. 79, No. 6, Mar. 15, 2007, pp. 2451-2462.
International Search Report and Written Opinion for International Application No. PCT/US2017/043876, dated Feb. 13, 2018 (14 pages).

* cited by examiner

*Primary Examiner* — Nicole Ippolito
*Assistant Examiner* — Hanway Chang
(74) *Attorney, Agent, or Firm* — Klarquist Sparkman, LLP

(57) ABSTRACT

Described herein are examples of systems and methods for integrating IMS and MS systems. In certain examples, systems and methods for decoding double multiplexed data are described. The systems and methods can also perform multiple refining procedures in order to minimize the demultiplexing artifacts. The systems and methods can be used, for example, for the analysis of proteomic and petroleum samples, where the integration of IMS and high mass resolution are used for accurate assignment of molecular formulae.

28 Claims, 17 Drawing Sheets

SYSTEMS AND METHODS FOR INTEGRATING ION MOBILITY AND ION TRAP MASS SPECTROMETERS

ACKNOWLEDGMENT OF GOVERNMENT SUPPORT

This invention was made with government support under DE-AC05-76RL01830 awarded by the U.S. Department of Energy. The government has certain rights in the invention.

FIELD

The disclosed technology relates to analytical instruments and, more particularly, to systems and methods for integrated ion mobility spectrometry and mass spectrometry systems.

BACKGROUND

Integrating ion mobility spectrometry ("IMS") systems and mass spectrometry ("MS") systems provides advantages in areas such as biomolecule analysis and characterization, national security, petroleum, and environmental monitoring. Despite its advantages, systems that integrate IMS and MS have shortcomings. Thus, improvements in this area are always desired.

SUMMARY

Complex samples benefit from multidimensional measurements with high resolution for full characterization of biological and environmental systems. To address this challenge, a drift tube-based IMS-Orbitrap MS device can be used. To circumvent the timing difference between the fast IMS separation and the slow Orbitrap MS acquisition, a dual gate and pseudo-random sequence ("PRS") can be used to multiplex ions into the drift tube and Orbitrap. The instrument can be designed to operate in signal averaging ("SA"), single multiplexing ("SM") and double multiplexing ("DM") IMS modes to fully optimize the signal-to-noise ratio of the measurements.

Described herein are examples of systems and methods for integrating IMS and MS systems. In some examples, the systems and methods can be used to analyze a sample containing a plurality of analytes.

In certain examples, systems and methods for deconvolution of DM data are described. The systems and methods can recover the SM data from the encoded DM data and then can decode the SM data. The systems and methods can also perform multiple refining procedures in order to minimize the demultiplexing artifacts. The systems and methods can be used, for example, for the analysis of proteomic and petroleum samples, where the integration of IMS and high mass resolution are used for accurate assignment of molecular formulae.

In one particular example, a method of analyzing a sample containing a plurality of analytes comprises introducing two or more ion packets comprising accumulated ions from the multiple analytes in the sample in succession from an ion funnel into a drift region of an ion mobility separation stage at time intervals that are other than constant and encoded by a first pulse sequence, separating ions in the two or more ion packets in the drift region of the ion mobility separation stage at each of the time intervals to obtain separation profiles therefore, releasing ions in the two or more separated ion packets with control circuitry from the drift region of the mobility separation stage through an ion gate into the ion trap mass spectrometer at time intervals encoded by a second pulse sequence, wherein the release of ions into the ion trap mass spectrometer is performed with a double multiplexing from which double multiplexed data is created, recovering single multiplexed data from the double multiplexed data, decoding the single multiplexed data to produce decoded data, and determining a species of the ions based on the decoded data.

In some examples, the act of recovering comprises a least squares projection technique, and a first basis space of the double multiplexed data is projected onto a second basis space of single multiplexed data. In some examples, the act of decoding comprises using an inverse simplex matrix.

In some examples, the mass spectrometer is an ion trap mass spectrometer. In some of those examples, the mass spectrometer is an Orbitrap mass spectrometer.

In some examples, the act of recovering comprises multiplying the double multiplexing data by an inverse matrix. In some examples, the method further comprises validating the single multiplexed data; and shifting an output of the validation to preserve accurate arrival times.

In some examples, the number of ion releases through the ion gate is defined by a binary term $2^N-1$ in the second pulse sequence where N is the number of data bits in the second pulse sequence. In some examples, the first pulse sequence is the same as the second pulse sequence. In other examples, the first pulse sequence is different than the second pulse sequence. In some examples, a length or duration of the first pulse sequence is the same as a length or duration of the second pulse sequence. In other examples, a length of the first pulse sequence is different than a length of the second pulse sequence.

In another particular example, a method of analyzing a sample containing a plurality of analytes comprises receiving double multiplexed data from a device, wherein the device comprises an ion mobility separation stage with a drift region therein coupled to an ion trap mass spectrometer, wherein the separation stage is configured to receive two or more ion packets comprising ions from multiple analytes in a sample in succession from an ion funnel trap at time intervals that are other than constant encoded by a first pulse sequence that separates the ions in the drift region therein, an ion gate disposed at an end of the drift region in front of the ion trap mass spectrometer, and control circuitry configured to release ions in two or more separated ion packets from the drift region through the ion gate into the ion trap mass spectrometer at time intervals encoded by a second pulse sequence within the acquisition time of the ion trap mass spectrometer, recovering single multiplexed data from the double multiplexed data, which comprises, generating a first matrix S, generating a second matrix A that includes the double multiplexed data, resizing the second matrix A to a third matrix R, generating a fourth matrix $S^T$, wherein $S^T$ is a transpose matrix of the first matrix S, and calculating $(S^T \times S)^{-1} \times S^T \times R$ to generate a fifth matrix, decoding the single multiplexed data, thereby producing decoded data, and determining a species of the ions based on the decoded data.

In some examples, the first matrix S comprises a size n×m and is generated from an encoding pseudo-random sequence, and wherein n is a length of the pseudo-random sequence and m=2*n−1. The first matrix S is a block diagonal matrix, and each diagonal block contains a reverse pseudo-random sequence. The second matrix A is a size k×l, and where k is a m/z dimension and l is a drift time dimension in scan numbers. In some examples, the method further comprises aligning each row of the second matrix A by finding a maximum intensity scan number and shifting each row via modulus. In some embodiments, the double multiplexed data is encoded by a pseudo-random sequence and an oversampling number which determines a number of segments per row, the number of segments is obtained by dividing a row count by a length of the oversampling number, and the third matrix R has a row count equal to the number of segments and a column count equal to the oversampling number. In some embodiments, the method further comprises resizing the fifth matrix to the row size of the second matrix A. In some embodiments, the method of claim 15, further comprising validating the product of the calculation. In some embodiments, the method further comprises shifting an output of the validation to preserve accurate arrival times.

In yet another example, a system comprises an ion mobility separation stage with a drift region therein coupled to an ion trap mass spectrometer, wherein the separation stage is configured to receive two or more ion packets comprising ions from multiple analytes in a sample in succession from an ion funnel trap at time intervals that are other than constant encoded by a first pulse sequence that separates the ions in the drift region therein, an ion gate disposed at an end of the drift region in front of the ion trap mass spectrometer, and control circuitry configured to release ions in two or more separated ion packets from the drift region through the ion gate into the ion trap mass spectrometer at time intervals encoded by a second pulse sequence within the acquisition time of the ion trap mass spectrometer, wherein the release of ions into the ion trap mass spectrometer is performed with a double multiplexing from which double multiplexed data is generated, wherein the control circuitry is configured to decode the double multiplexed data by projecting the double multiplexed data directly onto a basis space of a decoded signal and by transforming an inverse transform matrix by pre-multiplying the inverse transform matrix with an inverse simplex matrix.

The foregoing and other objects, features, and advantages of the invention will become more apparent from the following detailed description, which proceeds with reference to the accompanying figures.

DETAILED DESCRIPTION

General Considerations

Figure 1:
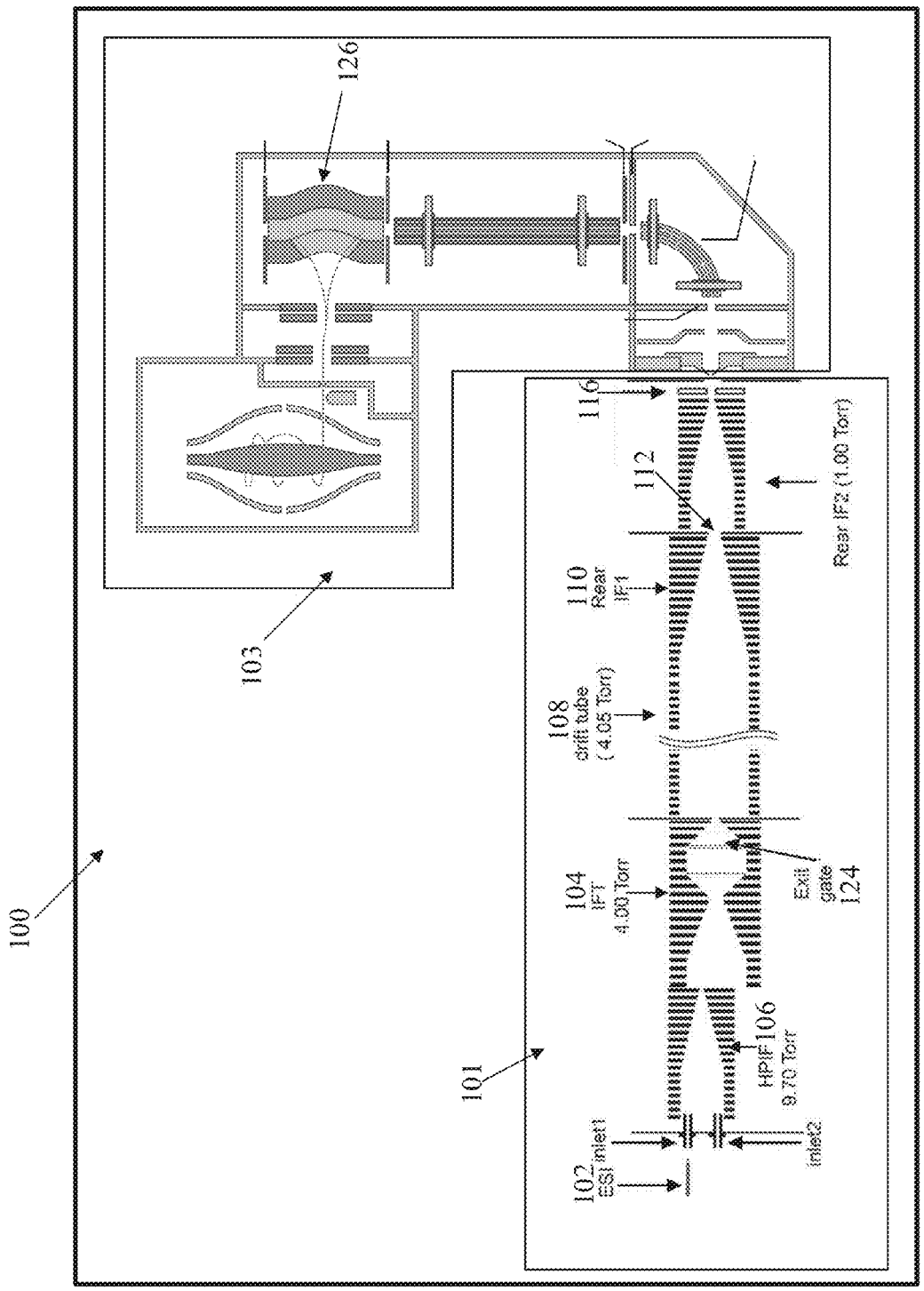
FIG. 1 illustrates an exemplary in integrated IMS-Orbitrap MS device as can be used in certain embodiments of the disclosed technology.

This disclosure is set forth in the context of representative embodiments that are not intended to be limiting in any way.

As used in this application and in the claims, the singular forms "a," "an," and "the" include the plural forms unless the context clearly dictates otherwise. Additionally, the term "includes" means "comprises."

The systems, methods, and apparatus disclosed herein should not be construed as being limiting in any way. Instead, this disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Furthermore, any features or aspects of the disclosed embodiments can be used in various combinations and sub-combinations with one another. Furthermore, as used herein, the term "and/or" means any one item or combination of items in the phrase.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged, omitted, or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "receive," "produce," "identify," "transform," "modulate," "calculate," "predict," "evaluate," "validate," "apply," "determine," "generate," "associate," "select," "search," and "provide" to describe the disclosed methods. These terms are high-level abstractions of the actual operations that are performed. The actual operations that correspond to these terms can vary depending on the particular implementation and are readily discernible by one of ordinary skill in the art.

Some of the disclosed methods can be implemented with computer-executable instructions stored on one or more computer-readable storage media (e.g., non-transitory computer-readable media, such as one or more volatile memory components (such as DRAM or SRAM), or nonvolatile memory components (such as hard drives) and executed on a computer. Any of the computer-executable instructions for implementing the disclosed techniques as well as any data created and used during implementation of the disclosed embodiments can be stored on one or more computer-readable media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer (e.g., any suitable commercially-available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well-known in the art are omitted. For example, it should be understood that the disclosed technology is not limited to any specific computer language or program. Likewise, the disclosed technology is not limited to any particular computer or type of hardware. Certain details of suitable computers and hardware are well-known and need not be set forth in detail in this disclosure.

Theories of operation, scientific principles, or other theoretical descriptions presented herein in reference to the systems, methods, and apparatus of this disclosure have been provided for the purposes of better understanding and are not intended to be limiting in scope. The systems, methods, and apparatus in the appended claims are not limited to those systems, methods, and apparatus that function in the manner described by such theories of operation.

Introduction to Disclosed Technology

Interest in IMS analyses in areas such as biomolecule analysis and characterization, national security, petroleum, and environmental monitoring has greatly increased over the last decade. IMS separates ions based on the balance between two forces that impact the ion movement, namely, the electric field and the drag force from the collision with buffer gas molecules. In some applications, the buffer gas can be inert. In other applications, a reactive buffer gas is desired. Different variations of the application of electric field and stationary state of the buffer gas have given rise to multiple IMS-based devices such as drift tube IMS ("DTIMS"), traveling wave IMS ("TWIMS"), trapped IMS ("TIMS"), overtone IMS ("OIMS"), differential IMS ("DIMS"), field asymmetric IMS ("FAIMS"), transversal modulation IMS ("TM-IMS"), etc. In classical DTIMS, ions travel through the drift tube under the influence of an attractive and weak electric field while colliding with a stationary buffer gas. Ions with small collisional cross section spend less time inside the drift tube while ions of larger collision cross sections spend more time. The collision cross section depends on the ion mobility (which depend on ion-neutral interaction potential), effective temperature and reduced mass. Thus, IMS provides information on the shape of molecules that cannot be readily accessible from MS information alone. IMS also separate species based on their charge state and their shape which in turn depend on the chemical makeup and spatial structure of the molecules. The signal of ions that exit IMS can be acquired using a simple charge collector (e.g., a Faraday plate) or using the more sophisticated mass spectrometer.

While early IMS analyses focused on using the technique as a standalone device to study ion-neutral interactions and separate small molecules, the field has broadened dramatically as IMS was integrated with mass spectrometers. The IMS-MS analyses opened new areas of research where the two-dimensional separation provided new capabilities to characterize the different aspects of ions in the gas phase. However, to preserve the IMS duty cycle while also accurately profiling the IMS separation, the acquisition rate of the mass spectrometer must be much faster than the IMS separation time. Since IMS normally distinguishes ions in a time scale of milliseconds, mass spectrometers such as time-of-flight ("TOF") MS are a natural fit. TOF MS samples ions on a microsecond time scale which allows a few points across an IMS peak forming a nested IMS-MS spectra. It is also desirable to integrate IMS with much slower trap-based instruments. Trap-based instruments provide advantages, for example, in terms of the much higher mass resolution and accuracy and ability to perform tandem MS analyses. Integrating IMS with slow detectors (such as ion trap-based MS) can incorporate a dual grid gating technique. This approach can be used to enable mass and mobility selected ion activation as well as for fast screening. The dual grid gating approach relies on a first grid to inject ions into the drift cell (to initiate the IMS experiment) and a second grid at the end of drift cell to allow ions of a specific arrival time to transmit to the detector. At constant delay times between the first and second grids, this approach allows continuous monitoring of specific ions (e.g., single ion monitoring). Alternatively, scanning the delay time between the first and second grids allows the construction of the whole IMS separation domain. This approach has the advantage of decoupling IMS speed from the acquisition speed of the detector or mass spectrometer, but it is slow due to the need to scan the entire mobility separation time and the long acquisition time of the mass spectrometer. Traditionally, IMS measurements utilize a single gate configuration which is very low duty cycle as only a narrow pulse of ions is admitted into the drift cell. Adding a second gate (as in the dual grid gating approach) lowers the IMS duty cycle even further. In an IMS separation time of 100 ms, the second gate allows a pulse of 200 μs to be transmitted to the mass spectrometer while discarding the rest of ions resulting in a duty of cycle of 0.2% at the second gate.

EXAMPLES

Generally speaking, the examples described herein are systems and methods for analyzing samples containing multiple analytes to determine both the separation time and mass to charge ratio (m/z) for each analyte. The systems comprises a separation device that separates the individual analytes by virtue of some physical and/or chemical characteristic other than the mass to charge ratio (m/z) of the analytes. The separation device is interfaced with a mass spectrometer, which then measures the mass to charge ratio (m/z) of the analytes. Additional details regarding sample analysis can be found, for example, in U.S. Pat. No. 9,269,548, which is incorporated by reference herein in its entirety.

Also described herein are examples of the application of the pseudo-random multiplexing scheme to the dual gates of an IMS-Orbitrap MS device to maximize the sampling of ions into the Orbitrap and to improve the signal-to-noise ratio of the measurements. Although these examples illustrate the analysis of complex analytes (e.g., proteomic samples and petroleum distillate fractions) to illustrate how the 2D separations provide higher peak capacity than each dimension alone, the described technology can be adapted to various other applications. It should be noted that although specific dimensions, operating parameters, etc. are provided in the examples disclosed here, the devices can comprise various other dimensions and/or operating parameters.

Figure 2:
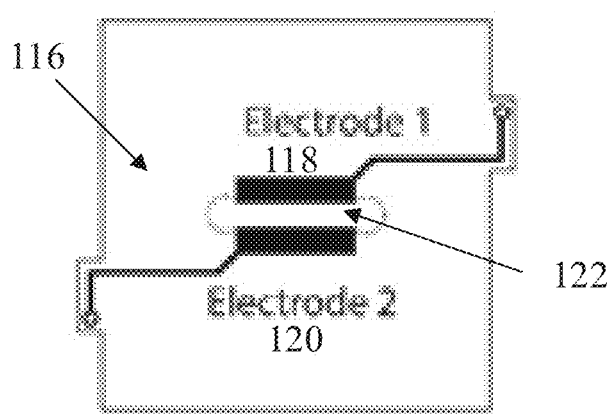
FIG. 2 is a detail view of a scan gate of the IMS-Orbitrap MS device of FIG. 1.

The methods described herein can, for example, be performed using an IMS-Orbitrap MS device 100, as shown in FIG. 1. The IMS-Orbitrap MS device 100 can comprise two main components: an IMS portion 101 and an Orbitrap MS portion 103. A few details of the IMS-Orbitrap MS device 100 are described herein, and additional details regarding the IMS-Orbitrap MS device 100 can be found, for example, in U.S. Pat. No. 9,269,548. The IMS-Orbitrap MS device 100 can, for example, form ions with an Electrospray Ionization Source ("ESI") 102. The ions can be transferred to an ion funnel trap ("IFT") 104 through a differentially pumped high pressure ion funnel 106 operating at 9.70 Torr. The ions can be trapped at 4.00 Torr in the IFT 104 for 4 ms and injected into a drift tube 108 in 200-300 μs pulses. The diffuse ions packets can travel through the 79-cm long and uniform field drift tube 108 and can be collected by a 15-cm long, 5 cm i.d. rear ion funnel (rear IF1) 110 operating at or about the same pressure as the drift tube 108 (e.g., 4.05 Torr). Ions can exit the rear IF1 110 through a 2.5 mm i.d. conductance limiting orifice 112 into a second rear ion funnel (rear IF2) 114 at a pressure of 1.00 Torr. The rear IF2 114 can be pumped, for example, using a pump that backs the Orbitrap turbo pumps (not shown). The rear IF2 114 can be about 10 cm long with an acceptance diameter of 2.5 cm and an exit orifice of 2.5 mm. The rear IF2 114 can be operated at a RF of 870 KHz and 100 Vp-p. A similar E/N (E is the field in V/cm and N is the number density) was maintained at about 4.5 V·cm$^{-1}$·Torr$^{-1}$ (e.g., about 14 Td) throughout the drift tube 108, rear IF1 110, and rear IF2 114. At the end of the rear IF2 114, a scan gate lens 116 can be used to modulate ion introduction to the Orbitrap portion 103. The scan gate 116 can be fabricated using printed circuit board technology by depositing a thin gold layer (e.g., about 65 μm) onto a 1.6 mm-thick nonconductive surface made from hydrocarbon ceramic (e.g., RO4000). As shown in FIG. 2, the scan gate 116 can comprise two electrodes 118, 120 separated by 4 mm gap 122 and can operate, for example, similarly to a Bradbury-Nielsen gate by applying different voltages to the two electrodes 118, 120 in order to block ion transmission and by applying the same voltages to transmit ions. To shield the scan gate 116 from the RF applied to the rear IF2 114 and downstream multipole, two DC-orifices of 3 mm i.d. can separate the scan gate 116 from the rear IF2 114 and a first multipole of the Orbitrap portion 103.

Since an Orbitrap portion 103 is a trapping instrument while IMS portion 101 is a pulsed technique, the IMS portion 101 can be synchronized with a curved linear trap ("C-trap") 126 of the Orbitrap portion 103. In non-IMS mode (e.g., continuous ion beam) ions can be initially injected into the C-trap 126 for a time period corresponding to the Automatic Gain Control ("AGC") injection time. When the desired injection time is reached, the C-trap 126 can close to incoming ions from the ESI 102, thereby allowing ions to be trapped and then injected into the Orbitrap portion 103 for detection. In IMS mode, ions can arrive at the Orbitrap portion 103 in packets or groups that are temporally separated. As such, the ion's arrive to the scan gate 116 and then to the C-trap 126 to reduce and/or prevent lost ions. Thus, a pulse from the C-trap 126 corresponding to the injection into the Orbitrap portion 103 can be chosen to be a trigger to initiate the IMS portion 101. The AGC injection time can be set (e.g., maximized) in order to increase the probability of the IMS ion packets arriving at the C-trap 126 while being open.

In one particular example, tryptically digested Bovine Serum Albumin and Enolase can be diluted in 50% Methanol:50% Water which can acidified with 0.1% formic acid. ESI positive ion calibration solution can be used without dilution. Petroleum distillate fractions can obtained and can be diluted to 1 mg/ml in Toluene/Methanol buffer and acidified with formic acid. Samples can be run in positive electrospray mode.

Data can be collected using software in raw format and can be converted to a Unified Ion Mobility Format ("UIMF") file using a conversion tool written in C#. UIMF format can allow relatively easy data visualization as heat maps, as well as integration with other bioinformatics data processing tools.

Figure 3:
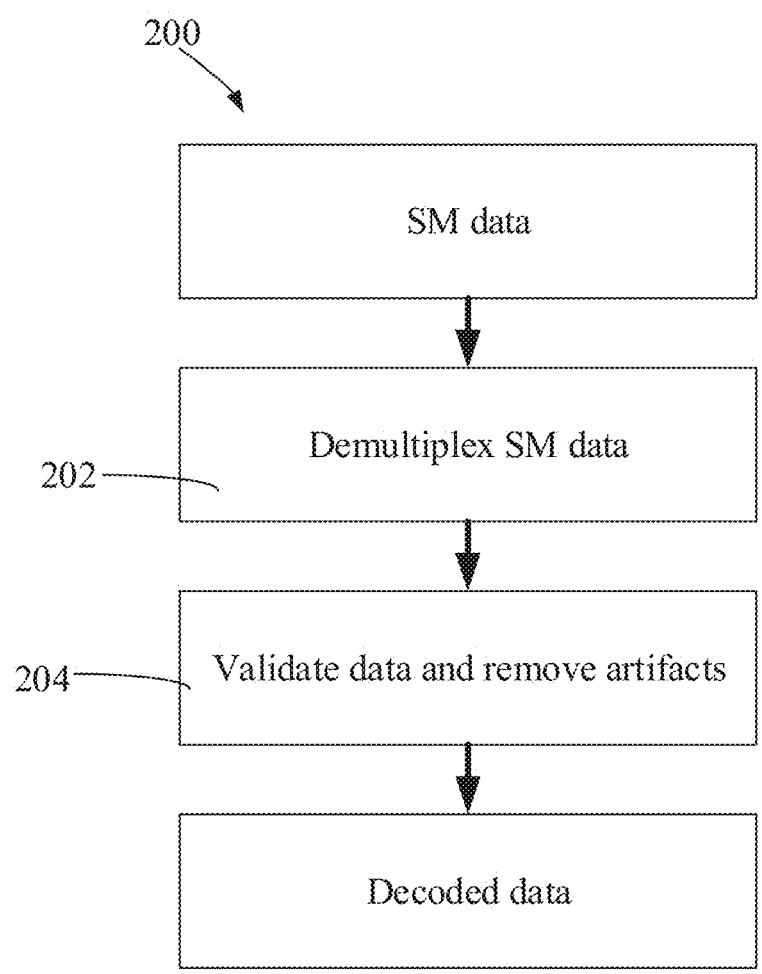
FIG. 3 is a flow chart that outlines an exemplary implementation of a method for decoding SM data as can be used in certain embodiments of the disclosed technology.

In one example, IMS data can be recovered from the SM data using a first method 200, as illustrated in FIG. 3. As illustrated by process block 202, first the SM data is demultiplexed based on the construction of the simplex matrix which is a square matrix of size n×n where n is the length of the pseudo-random sequence and the columns of the matrix are the elements of the pseudo-random sequence vector cyclically shifted. Following demultiplexing, a validation and artifact removal step is applied, as illustrated by process block 204. In other words, the first method applies analytical tests to validate whether a real signal or an artifact exists in the data and then uses a scoring mechanism to find each real signal and preserve it.

Unlike the "inverse simplex matrix" typically used in "Hadamard" multiplexing approach, the transformation matrix that encodes the original signal into the DM data is not cyclic, not symmetrical, nor directly invertible. Thus, decoding DM data cannot be done with typical methods or techniques. Additional information regarding Hadamard-transformed data can be found, for example, in U.S. Patent Application Publication No. 2014/0025314, which is incorporated by reference herein in its entirety.

Figure 4:
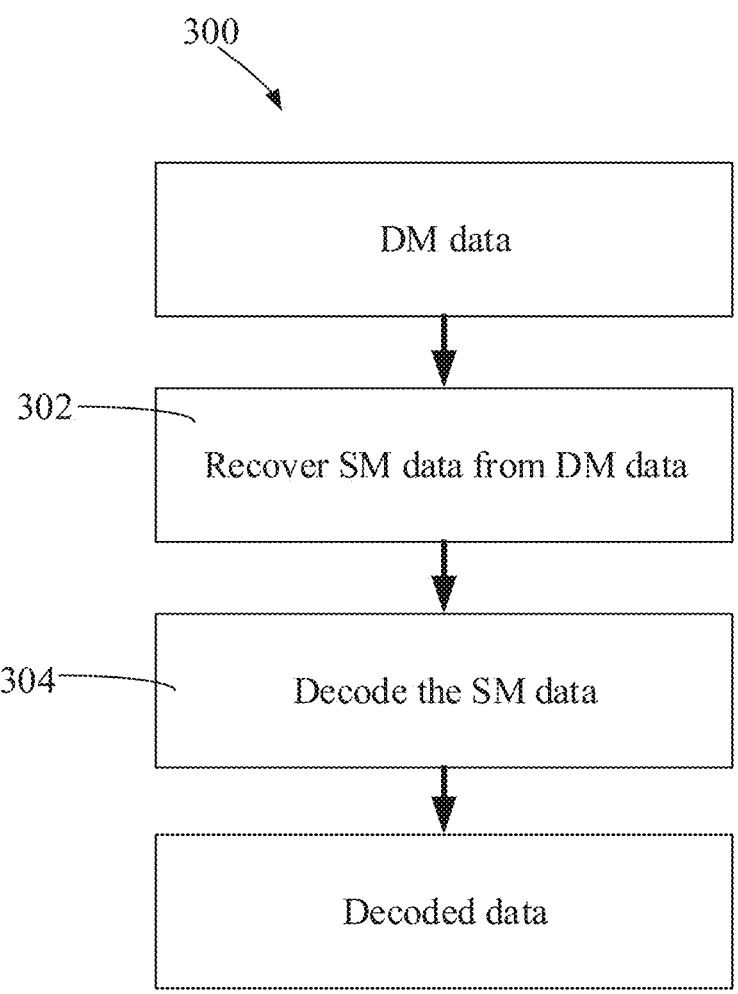
FIG. 4 is a flow chart that outlines an exemplary implementation of a method for decoding DM data as can be used in certain embodiments of the disclosed technology.

Described herein are methods that can decode DM data. In one example, a second method 300 can be used to decode DM data, as illustrated in FIG. 4. The second method 300 can comprise two main steps. In a first step, SM data that was used to construct the DM data can be recovered from the DM data, as illustrated in process block 302. A second step involves decoding the single multiplexed data, as illustrated by process block 304. To recover the SM data the raw encoded DM data is multiplied by an inverse matrix. A matrix S of size n×m is generated from the encoding pseudo-random sequence, where n is the length of the pseudo-random sequence and m=2*n−1. Note that S is a block diagonal matrix where each diagonal block contains the reverse pseudo-random sequence. The DM data acquired from the instrument is a matrix, A, of size k×l, where k is the m/z dimension and l is the drift time dimension in scan numbers. Each row of A is aligned by finding the maximum intensity scan number and subsequently shifting the row via modulus. The alignment permits peak correctness validation by shifting the DM data in such a way where the demultiplexed peak(s) will occupy the same scan numbers. For each row, the data is encoded by the pseudo-random sequence and an oversampling number which determines the number of segments per row vector. The number of segments is obtained by dividing the row count by the length of the oversampling. Each row (or vector) of matrix A is then resized into a matrix, R, that has a row count equal to the number of segments and a column count equal to the oversampling. The inverse of S is computed and the demultiplexed data is obtained by $D=(S^T \times S)^{-1} \times S^T \times R$. The result is then resized to the size of the row count of A and then validation is performed on the demultiplexed row. The output from validation is then shifted back to preserve accurate arrival times. This results in the decoded data.

Stated another way, in the first step 302, the DM data (with dual encoding, one at the IMS gate and other at the scan gate 116) can be deconvoluted once to obtain the singly encoding signal. To deconvolute from DM to SM data sequence, the convolution matrix that contains the two encoding sequences can be used. The SM data can be obtained using a least squares projection technique, where the basis space of the DM data can be projected onto the basis space of SM data. This inverse transformation matrix can be applied on the DM data to obtain the SM data. The second step 304 involves fully deconvoluting the signal by using a first inverse simplex matrix (e.g., from the Hadamard Transform technique) to the resulting data from the first step 302 giving rise to the decoded signal with much improved signal-to-noise ratio.

Figure 5:
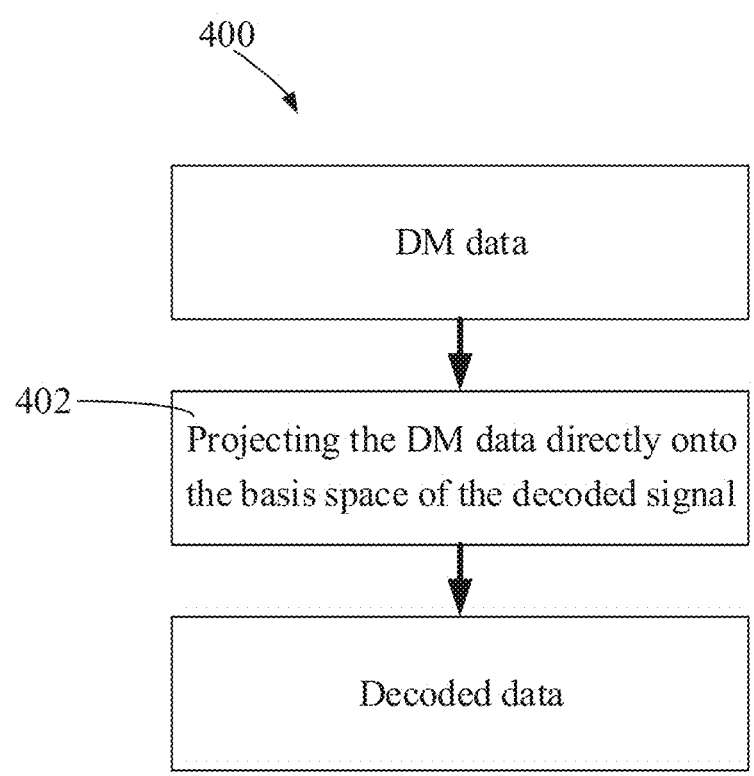
FIG. 5 is a flow chart that outlines an exemplary implementation of a method for decoding DM data as can be used in certain embodiments of the disclosed technology.

A third method 400 can be used to decode DM data, as illustrated in FIG. 5. The third method 400 can comprise projecting the DM data directly onto the basis space of the decoded signal. The inverse transform obtained from the second method 300 is further transformed by pre-multiplying it with a second inverse simplex matrix (i.e., the second inverse simplex matrix being different than the first inverse simplex matrix described above with respect to the Hadamard technique). The net transformation function when applied to the DM data yields the deconvoluted signal with greatly improved signal to noise ratio. Compared to the second method 300, which comprises two steps 302, 304, the third method 400 comprises a single step 402 to decode the data.

For example, the step 402 of the third method 400 can comprise a least squares projection technique, and a first basis space of the DM data can be projected onto a second basis space of a signal domain. In one particular example, the step 402 comprises generating a matrix S that includes SM data, generating a matrix $S^T$, wherein $S^T$ is a transpose matrix of the matrix S, generating a matrix C that is a simplex matrix, generating a matrix A that includes DM data, resizing the matrix A to a matrix R (e.g., similar to the manner described above with respect to the second method 300), and calculating $(S^T \times S \times C)^{-1} \times S^T \times R$ to generate a matrix D that includes the decoded data.

The methods 300, 400 can provide several significant advantages with handling DM data, which applies a pseudo-random sequence at the two gates before and after IMS separation. For example, the second method 300 can reduce and/or eliminate artifacts in the data and/or provides the highest signal-to-noise ratio of all modes (e.g., SA, SM, and DM), as further described below. The decoded data can then be used to determine one or more species of the ions from the sample.

In addition to operating the IMS-Orbitrap MS device 100 in continuous mode, e.g., where IMS is disabled and the instrument is operated as an Orbitrap-only instrument, the IMS-Orbitrap MS device 100 can also be operated IMS modes such as SA, SM, and DM. Examples of each are further described below.

Figure 6:
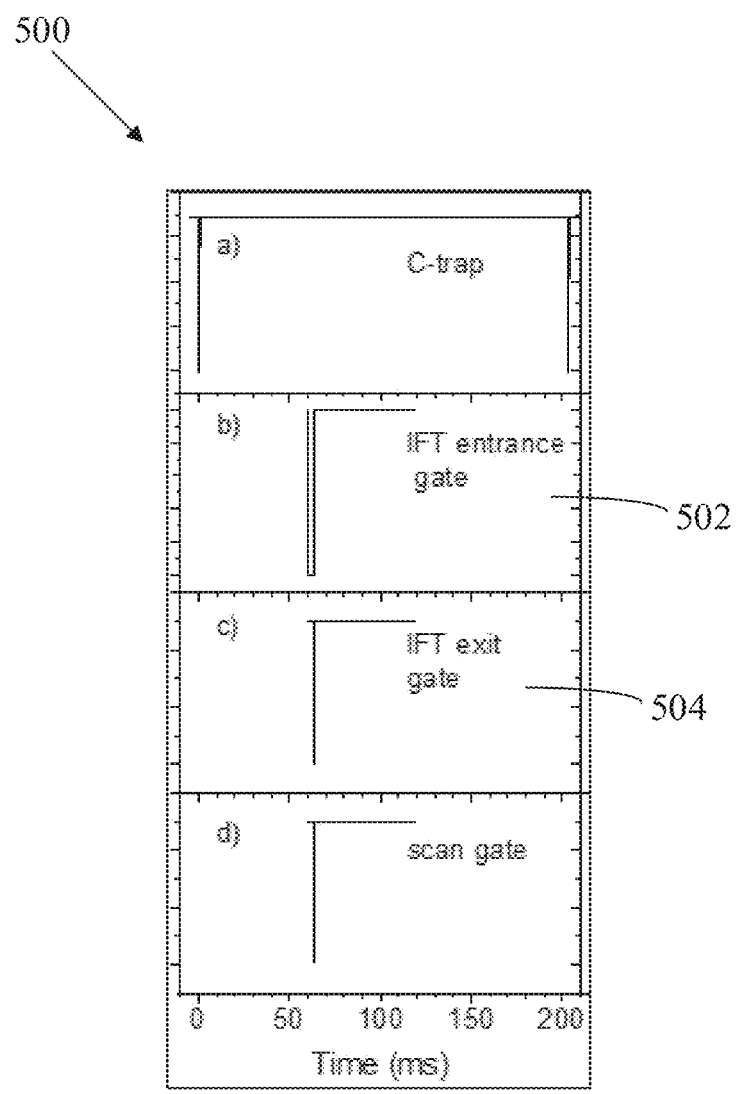
FIGS. 6-19 are charts illustrating parameters and characteristics as can be used and/or obtained in certain embodiments of the disclosed technology.

FIG. 6 illustrates an example timing sequence 500 from a SA mode of operation. In the SA mode of operation, ions can be stored in the IFT 104 (FIG. 1) by controlling the timing of the IFT entrance gate, as shown at 502. Following ion storage, the voltage on the exit gate can be lowered for 200-300 μs to inject a single ion packet into the drift tube where the ions separate according to their mobilities, as shown at 504. A voltage can then be applied to one of the scan gate electrodes to either transmit or block ions from passing into the C-trap 126. The length of the scan gate pulse (e.g., 200 μs) can be the portion of the total IMS separation (e.g., 60 ms) which is sampled by the Orbitrap portion 103. By sequentially stepping the delay time between pulses applied to the scan gate 116 (FIG. 1) and to an IFT exit gate 124, the entire IMS separation can be sampled. For example, 300 steps can be required to sample a 60 ms IMS separation time using a scan gate sweep rate of 200 μs/Orbitrap scan and a 200 μs wide scan gate pulse. Drift time can be calculated from the number of scan gate steps multiplied by the scan gate sweep rate.

Figure 7:
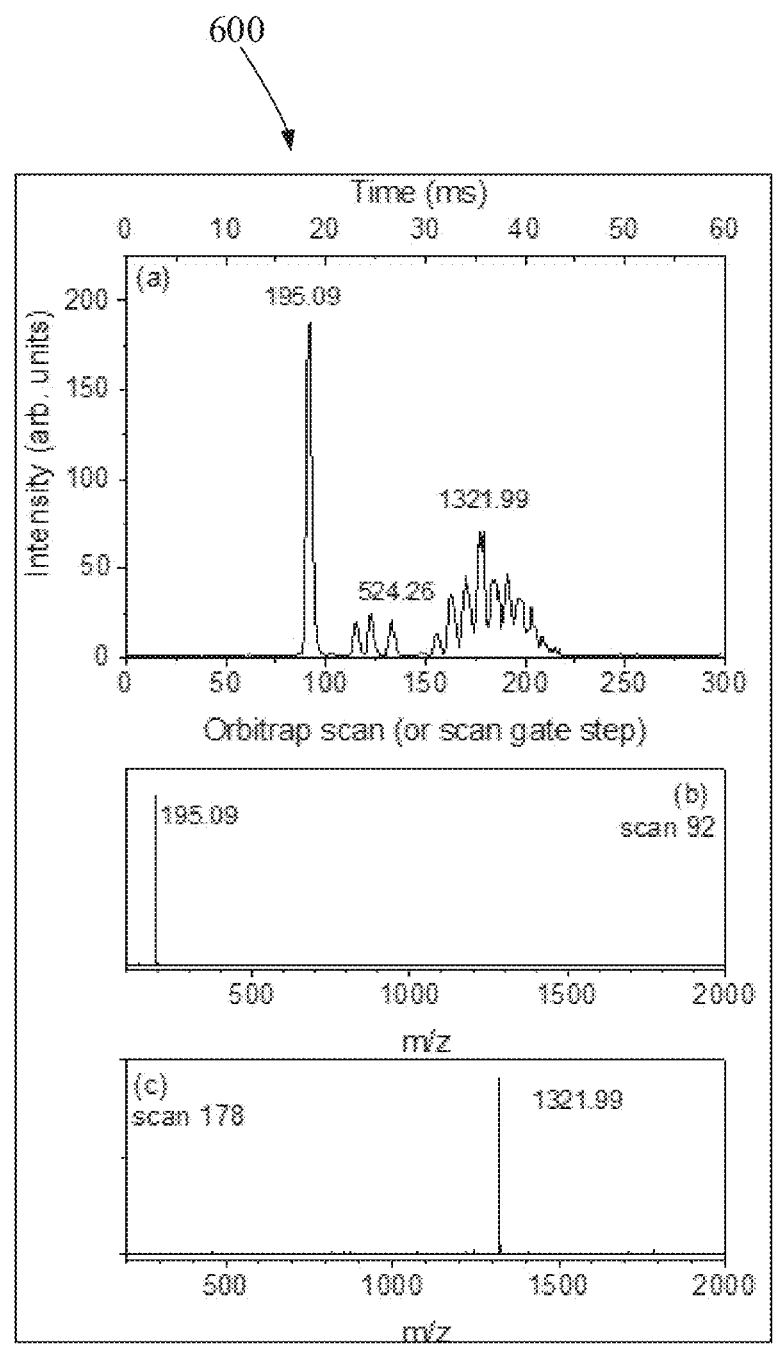

FIG. 7 shows an example chart 600 of IMS separation for singly charged species from the calibration solution. Total experiment time can depend on how fast the Orbitrap portion 103 can acquire data which in turn depends on the mass resolving power desired. In this example, a setting of 25,000 mass resolving power for the Orbitrap portion 103 can be used. As a result, 300 scan gate steps were completed in 1 minute. At 100,000 mass resolving power, the acquisition time can be about 5 minutes (e.g., for the MS). Reducing the number of scan gate steps by scanning over the useful IMS range can reduce the total time to about 30 seconds (e.g., for 25,000 mass resolving power). While the speed of the Orbitrap portion 103 is fixed, the ion utilization efficiency can be improved. One way to maximize ion utilization is to multiplex ion packets introduction into the IMS drift tube 108.

Figure 8:
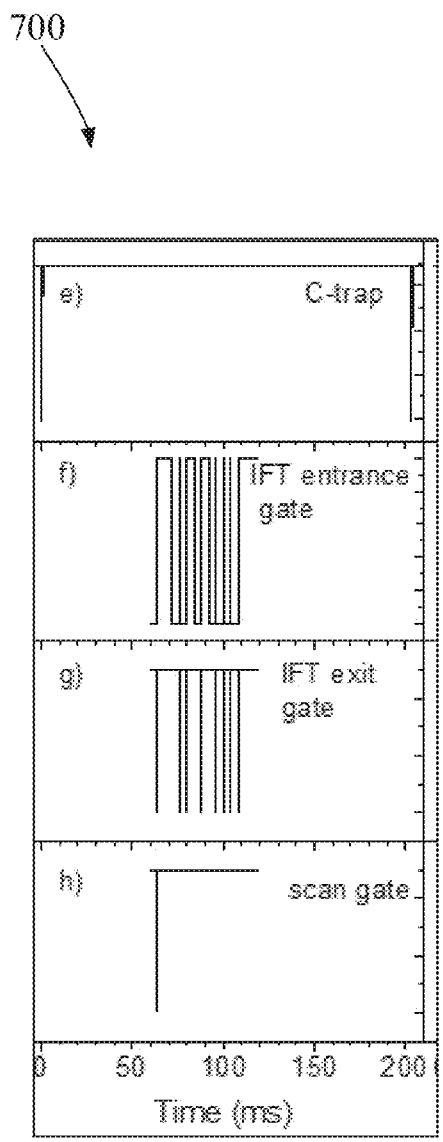

FIG. 8 illustrates an example timing sequence 700 from a SM mode of operation. In the SM mode, a pseudo-random sequence is applied to the IFT exit gate 124 in order to improve the IMS duty cycle by sequentially injecting multiple ion packets into the drift tube 108 for 60 ms (e.g., the same time as a SA experiment). Ion packets of different m/z may overlap in the drift tube 108 as their mobilities differ but ion packets of the same mobility do not overlap and stay separated at the end of the drift tube 108. Utilizing mathematical transformation on the encoded data, the IMS peaks can be decoded with improved signal-to-noise ratio.

Figure 9:
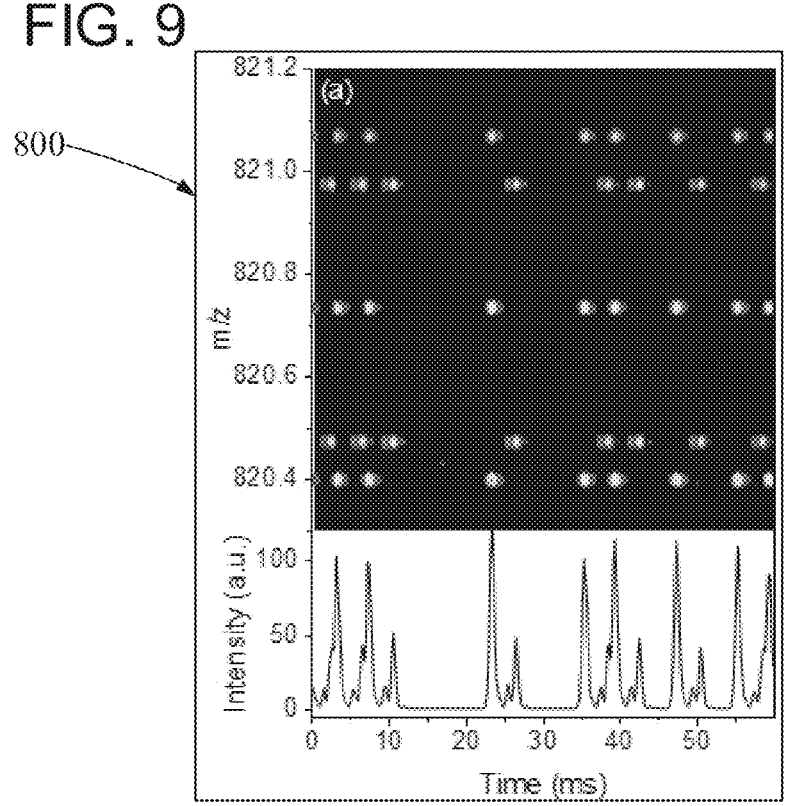

In the SM mode, the scan gate 116 transmits ions only once per Orbitrap scan, as shown in FIG. 8. In SM mode utilizing a 4-bit sequence, eight ion packets can be sampled by the scan gate 116. For example, FIG. 9 shows an example chart 800 illustrating an SM experiment a for mass-to-charge ratio ("m/z") region 820.3-821.2 from the tryptic digest of a BSA and Enolase mixture. A pseudo-random sequence of 100110101111000 can be utilized where a 1 represents an event of ion packet release while 0 represent no ion packet release into the drift tube 108.

Figure 10:
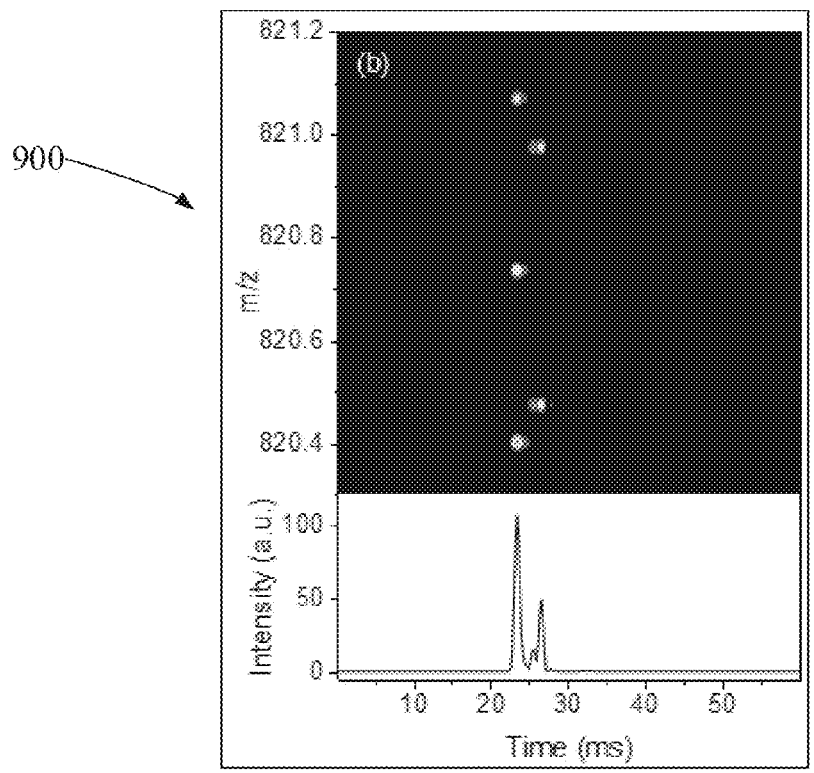

FIG. 10 shows an example chart 900 illustrating demultiplexed or decoded data with the correct IMS separation. In the SM scheme, the signal quality improves as compared to the SA scheme due to the larger number of ion packets being sampled as well as the reduction in random noise. SM also minimizes the IFT overfilling and undesirable space charge peak broadening effect by limiting the trap time to 4 ms for the 4-bit multiplexing.

Despite the increased number of ion packets being injected into the drift tube 108, the scan gate 116 samples each of these packets only once for every Orbitrap scan. Alternatively, the scan gate 116 can be operated more than one time per Orbitrap scan. For instance, the same multiplexing sequence applied to the IFT 104 can be also applied to the scan gate 116.

Figure 11:
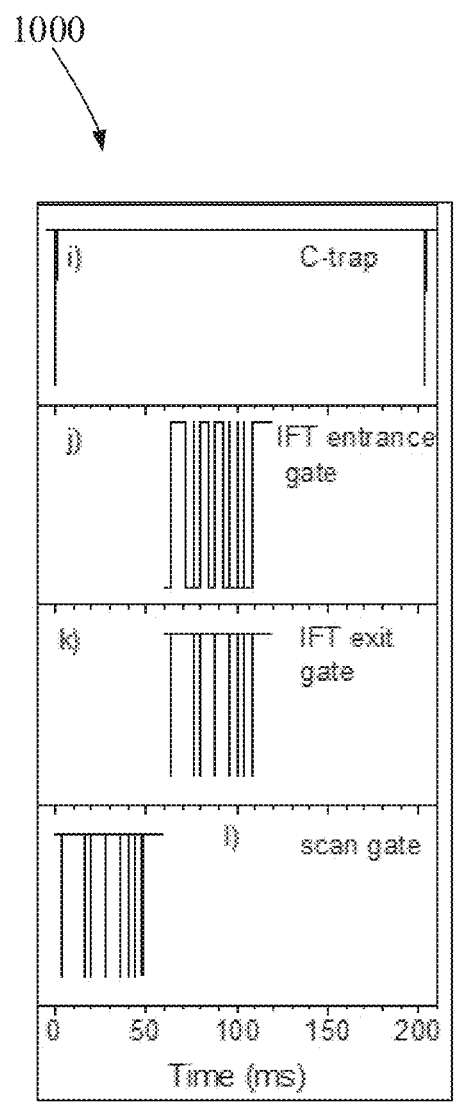
Figures 12, 13:
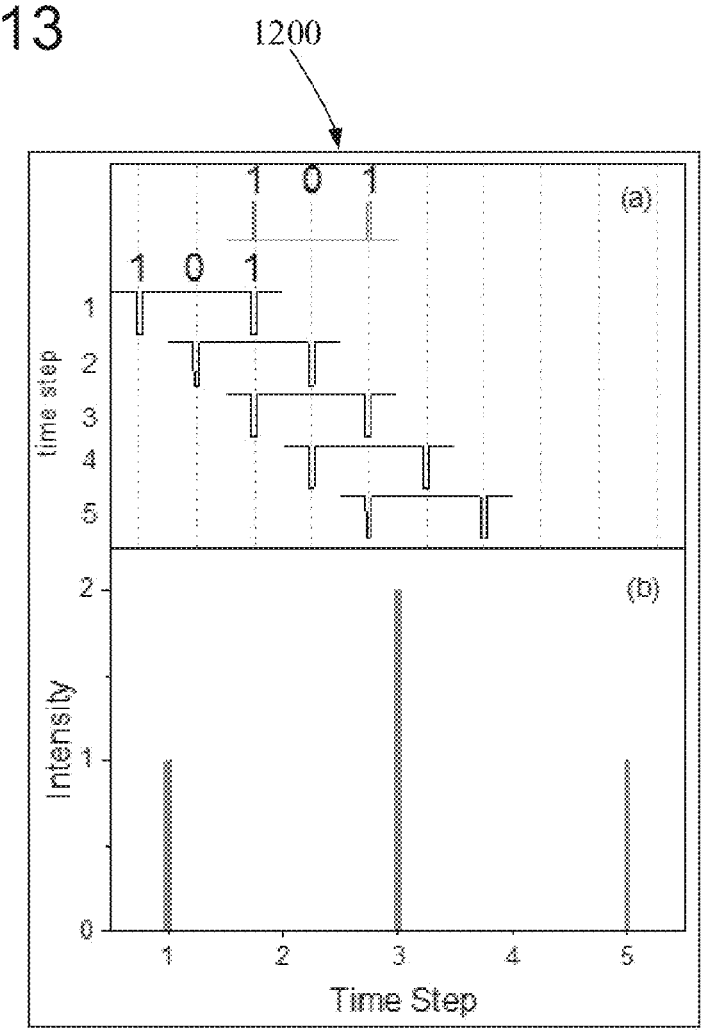

FIG. 11 illustrates an example timing sequence 1000 from a DM mode of operation, where the same pseudo-random sequence is applied to the IFT 104 and scan gate 116. In this case, the scan gate 116 transmits multiple ion packets for every Orbitrap scan. The resulting arrival time distribution then corresponds to the various combinations of multiplexing the IFT 104 and the scan gate 116. To illustrate this operation, assume for simplicity, a 2-bit multiplexing sequence (represented as 101 sequence) where two ion packets are released from the IFT and injected into the drift tube 108. In the 101 sequence, the two released ion packets are separated by 0, i.e., a no ion packet release event. Applying the same sequence of 101 to the scan gate 116 yields the results illustrated in charts 1100 and 1200, shown in FIGS. 12 and 13, respectively. Depending on the delay time between the IFT exit gate 124 and scan gate 116 an ion packet can be blocked (0) or transmitted (1) to the Orbitrap portion 103. In the first acquisition cycle (i.e. time step 1), the first ion packet (i.e. status of 1) from the IFT 104 arrived when the scan gate 116 is in the second transmission event (i.e. status of 1) therefore a signal of 1 can be detected in the first scan of the Orbitrap portion 103. In the second Orbitrap scan, the scan gate 116 is stepped to time step 2, where the first packet has arrived, while the scan gate 116 is closed, followed by the scan gate 116 in an open state (1) but with no ions arriving (0) from the IFT 104. The net result of time step 2 is no ions can be detected. The third Orbitrap scan corresponds to exact alignment between the two ion packets arriving at the scan gate 116 while in the transmission status resulting in two ion packets being transmitted to Orbitrap portion 103. The result is a packet of 2× ion intensity as compared to that resulting from step 1. The fourth and fifth time-steps result in no signal (0) and one packet transmitted (1), respectively. The final chromatogram will have five peaks of intensities of 10201 corresponding to the five scan gate steps.

Figure 14:
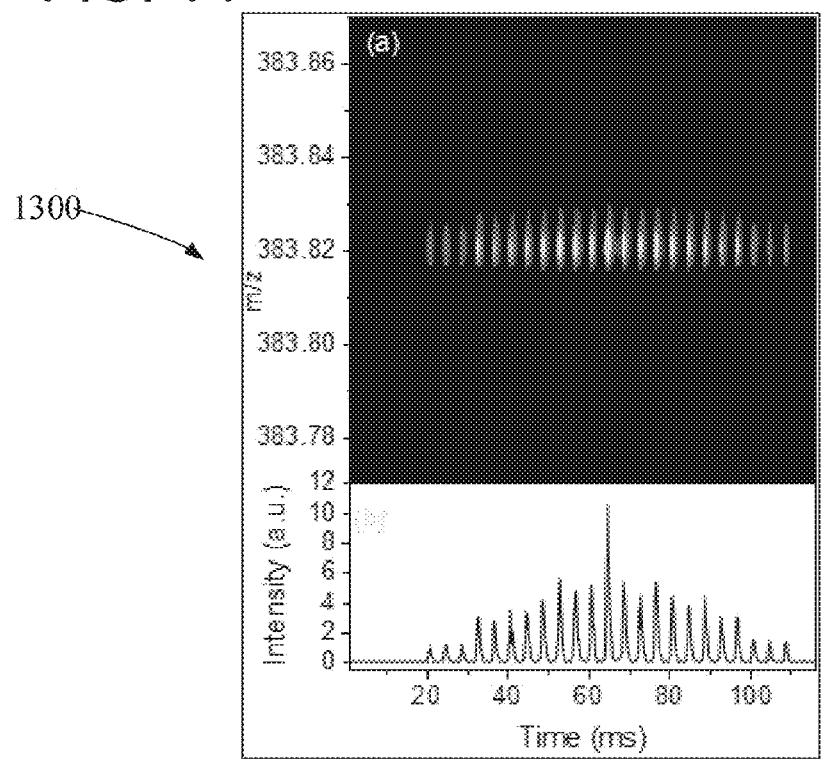
Figure 15:
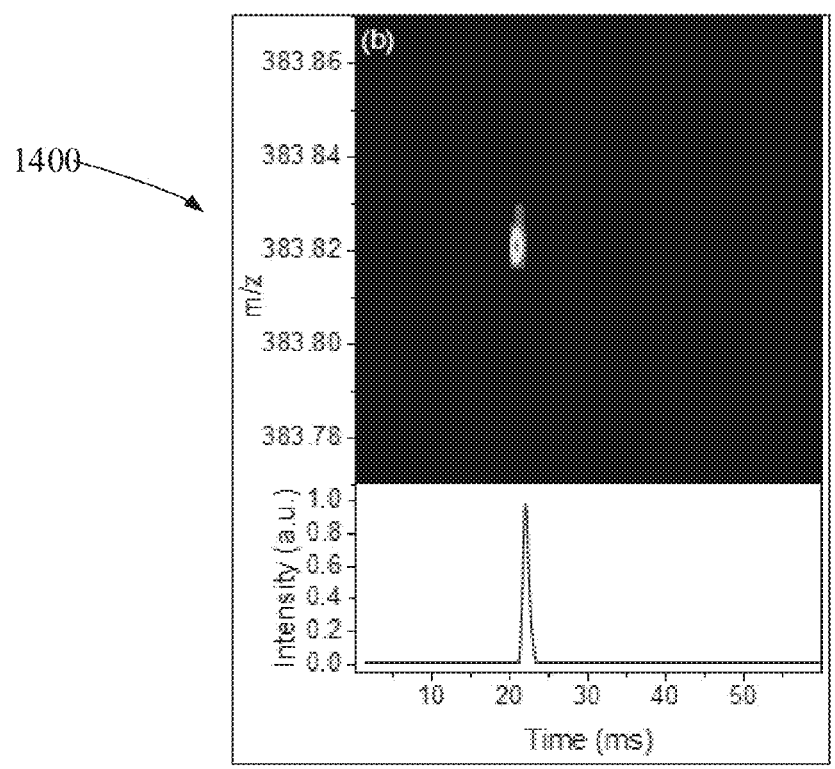

Similarly, in the case of 4-bit multiplexing sequence (100110101111000) applied to the IFT and to the scan gate, for example, the resulting distribution detected in Orbitrap scans will have intensity distributions that scale as 000111223334448444333221110000. The results of the DM demultiplexing are shown in FIGS. 14-15. FIG. 14 shows a chart 1300 illustrating the encoded data for a peak from a sample of heavy gas oil while FIG. 15 shows a chart 1400 illustrating the corresponding demultiplexed data. The advantage of the DM mode is the increase in ions' sampling into the Orbitrap portion 103 which can be (for a 4 bit sequence) 8 times higher than the SM mode and 64 times higher than the SA approach. The quality of the data from the DM mode can depend on the minimization of demultiplexing artifacts and reasons that contribute to them. For instance, signal variations due to ion source instability and insufficient ion statistics can lead to signal artifacts which can affect the quality of signal from DM data. Also, the ability of the demultiplexing method to confidently distinguish real signal from artifacts can improve the DM approach.

Figure 16:
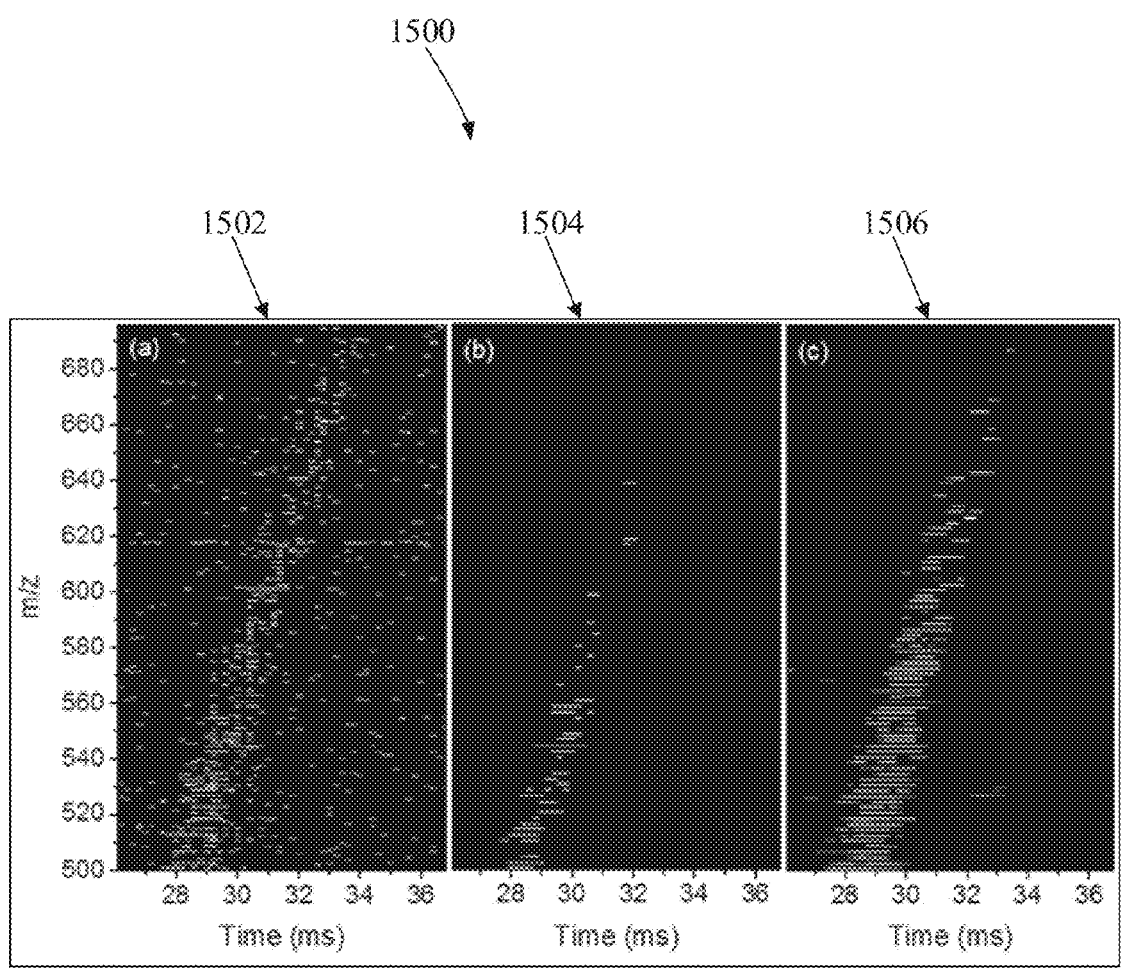

For example, FIG. 16 shows a chart 1500 illustrating SA 1502, SM 1504, and DM 1506 for an analysis of a heavy gas oil sample. FIG. 16 shows a comparison between the three modes for a selected m/z region (i.e., 500-680 m/z) of low abundance peaks to demonstrate the advantages of multiplexing. It is clear that DM 1506 has more peaks than SM 1504 which in turn has more peaks than SA 1502 due to the increased sampling of ions by DM 1506>SM 1504>SA 1502. Note the noise level in the demultiplexed spectra (i.e., SM 1504 and DM 1506) is essentially eliminated as compared to the SA 1502 mode which is key to high quality features in the multiplexing modes.

Figure 17:
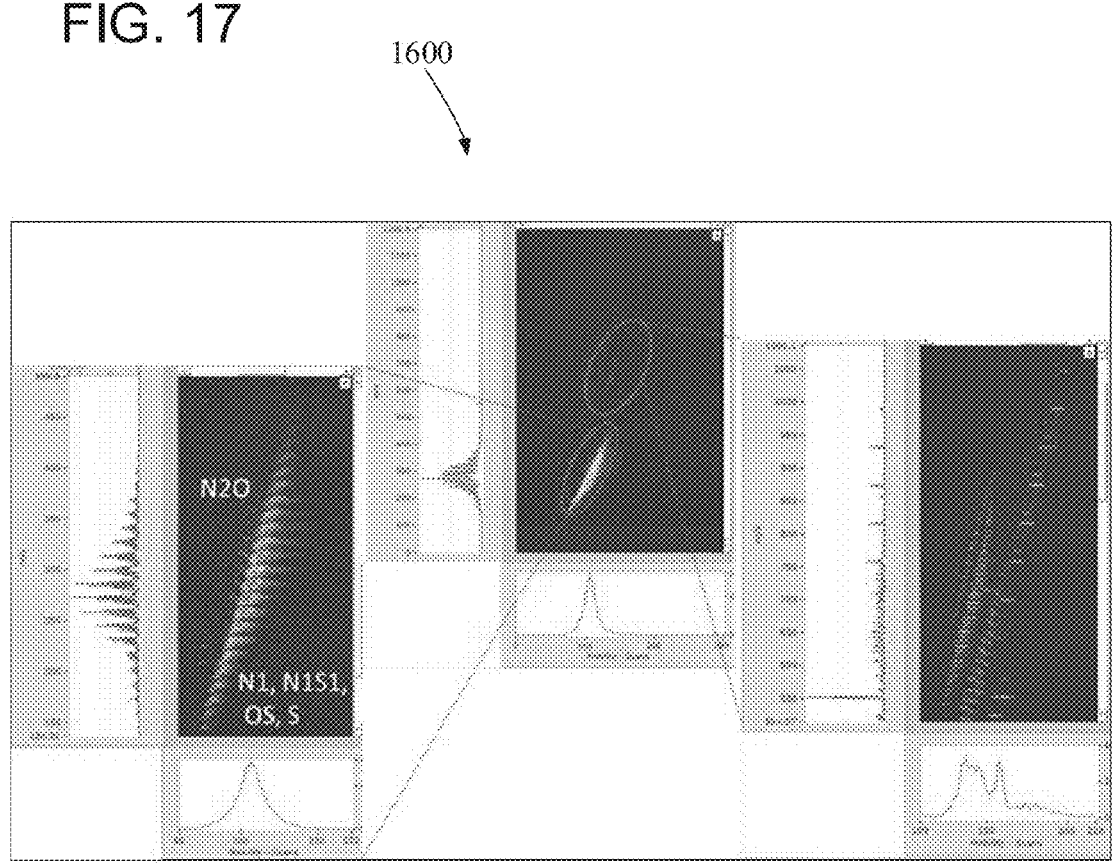
Figure 18:
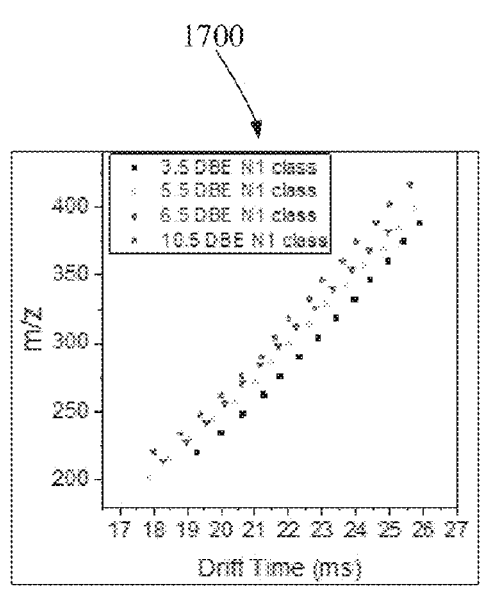

An example of a vacuum and hydrotreated gas oil sample is illustrated by a chart 1600, as shown in FIG. 17. In certain embodiments, a maximum mass resolving power of the Orbitrap portion 103 can be 100,000. There are distinct IMS-MS profiles for the different samples analyzed showing the utility of the IMS to visually distinguish different distillates. Data in FIG. 16 can be divided into two regions where each region is characterized by unique diagonal lines, or trend lines, on the IMS-MS heat map. These trend lines correspond to a different class of compounds that share core common structures or charge states. Focusing on the Gaussian mass distribution around approximately 280 m/z show a singly charged species that can be identified as N, NS, OS, S and $N_2O$ homologues series for the trend lines illustrated in chart 1700, as shown in FIG. 18. In the example, identifications were made with a mass measurement accuracy of ≤1 ppm. Each of these trend lines comprises homologous series members that differ by $CH_2$— and the trend line corresponds to structural growth of the homologous series for each additional $CH_2$. Notice that the long trend lines also include shorter sub-trend lines with different slopes. Considering only the N series these sub-trend lines correspond to the change in double bond equivalence number ("DBE"). FIG. 18 shows the multiple trend lines for a selected DBE. For ions of similar m/z, every additional double bond results in compactness of the carbon-carbon backbone. So ions of higher DBE are generally more compact and thus have higher mobilities. The trend lines can be used to correctly assign the molecular formulae to peaks by ensuring that these peaks fall into their correct trend lines. IMS also aids in resolving peaks of close m/z values.

Figure 19:
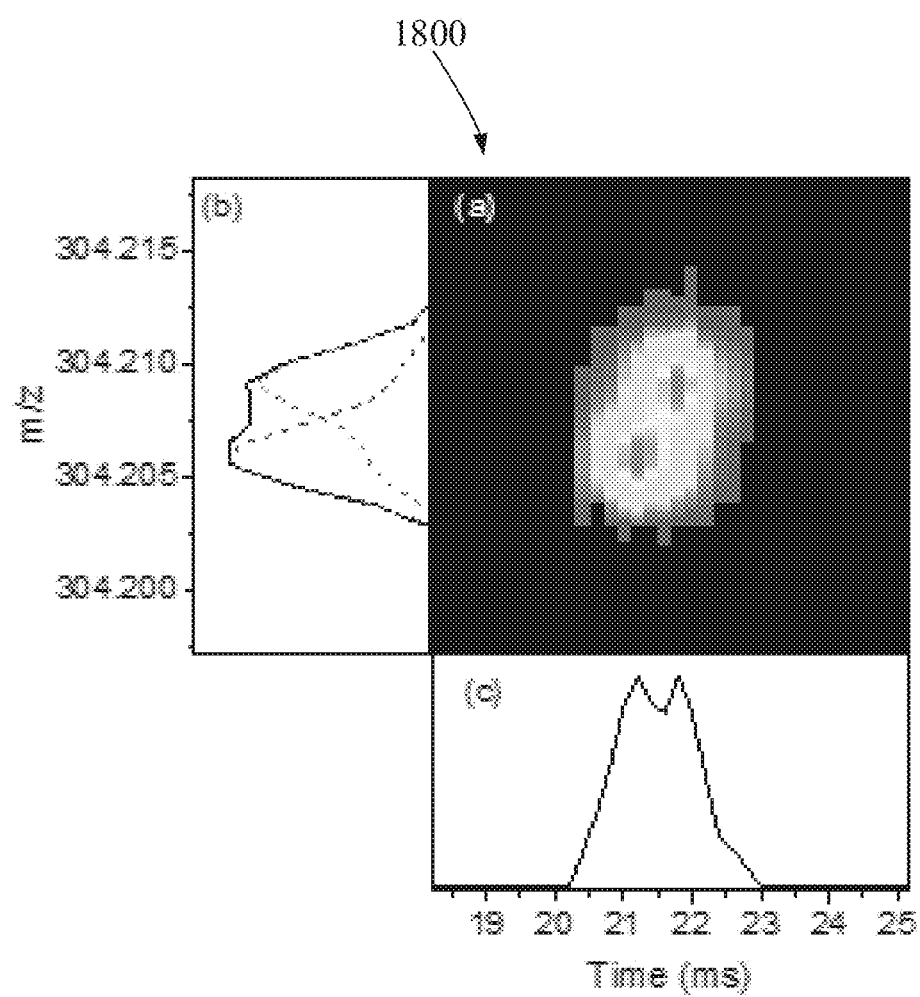

FIG. 19 shows a chart 1800 illustrating an example of two peaks that were partially resolved by the 100,000 mass resolving power of Orbitrap portion 103 and IMS portion 101 alone. However, by both dimensions together are nicely separated as shown by selecting the mass spectra collected at arrival times of 20.8 and 22.4 ms. The two peaks were assigned to m/z 304.20584 and 304.20917 of molecular formula $C_{22}H_{26}N$ and $C_{19}H_{30}NS$, respectively. The difference between the two peaks is only 3.33 mDa corresponding to the difference between $SH_4$ and $C_3$. This small difference is very common due to the many constituents in petroleum sample indicating the power of the IMS-Orbitrap MS device 100 for complex samples.

As illustrated and described, in all three modes the IMS-Orbitrap MS device 100 can acquire a 60 ms IMS separation in as little as 1 min for 25,000 mass resolving power and 5 min for the 100,000 mass resolving power with the duty cycle corresponding to the acquisition speed of the Orbitrap portion 103, desired mass resolution, and the sweep window and rate of the scan gate 116. The IMS-Orbitrap MS device 100 can accurately assign molecular formulae with overlapping peaks in the MS dimension for complex samples.

Figure 20:
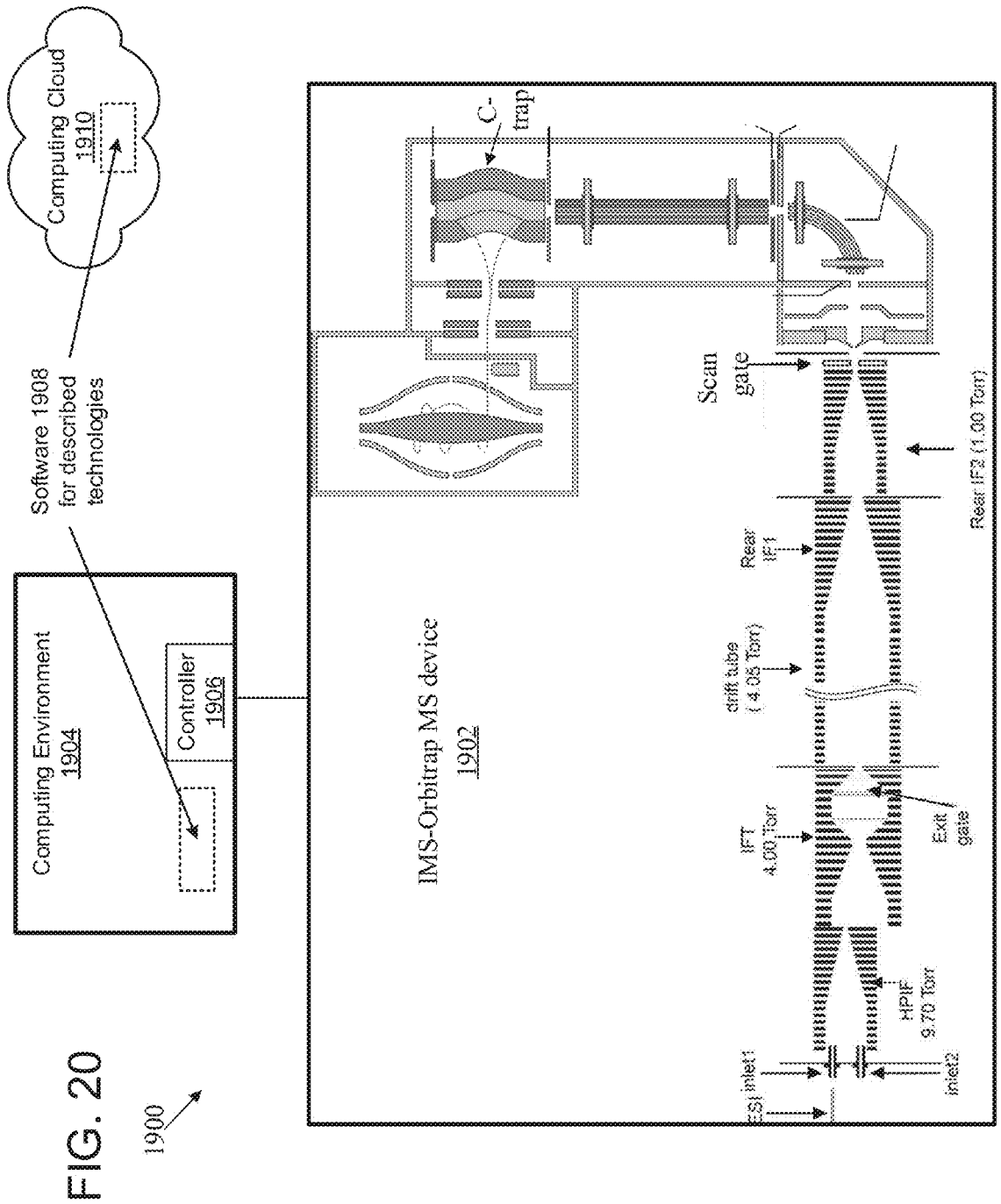
FIG. 20 illustrates an exemplary integrated IMS-Orbitrap MS system as can be used in certain embodiments of the disclosed technology.

FIG. 20 illustrates a system 1900 comprising an IMS-Orbitrap MS device 1902 (e.g., similar to the IMS-Orbitrap MS device 100 shown in FIG. 1) coupled to a computing environment 1904 with a controller 1906, as can be used in certain examples of the disclosed technology. The computing environment 1904 includes one or more processors, memory, and computer-readable storage media that can store software 1908 for implementing the disclosed technologies. In some examples, at least a portion of the software 1908 can be stored and/or executed in a server or a computing cloud 1910 at a location remote from the IMS-Orbitrap MS device 1902. In some examples, field programmable gate arrays (FPGAs) or other reconfigurable logic devices can be used to augment, or instead of, the processors and/or memory. The computing environment can include some or all aspects of the computing environment 2000 as described below and illustrated in FIG. 21.

Figure 21:
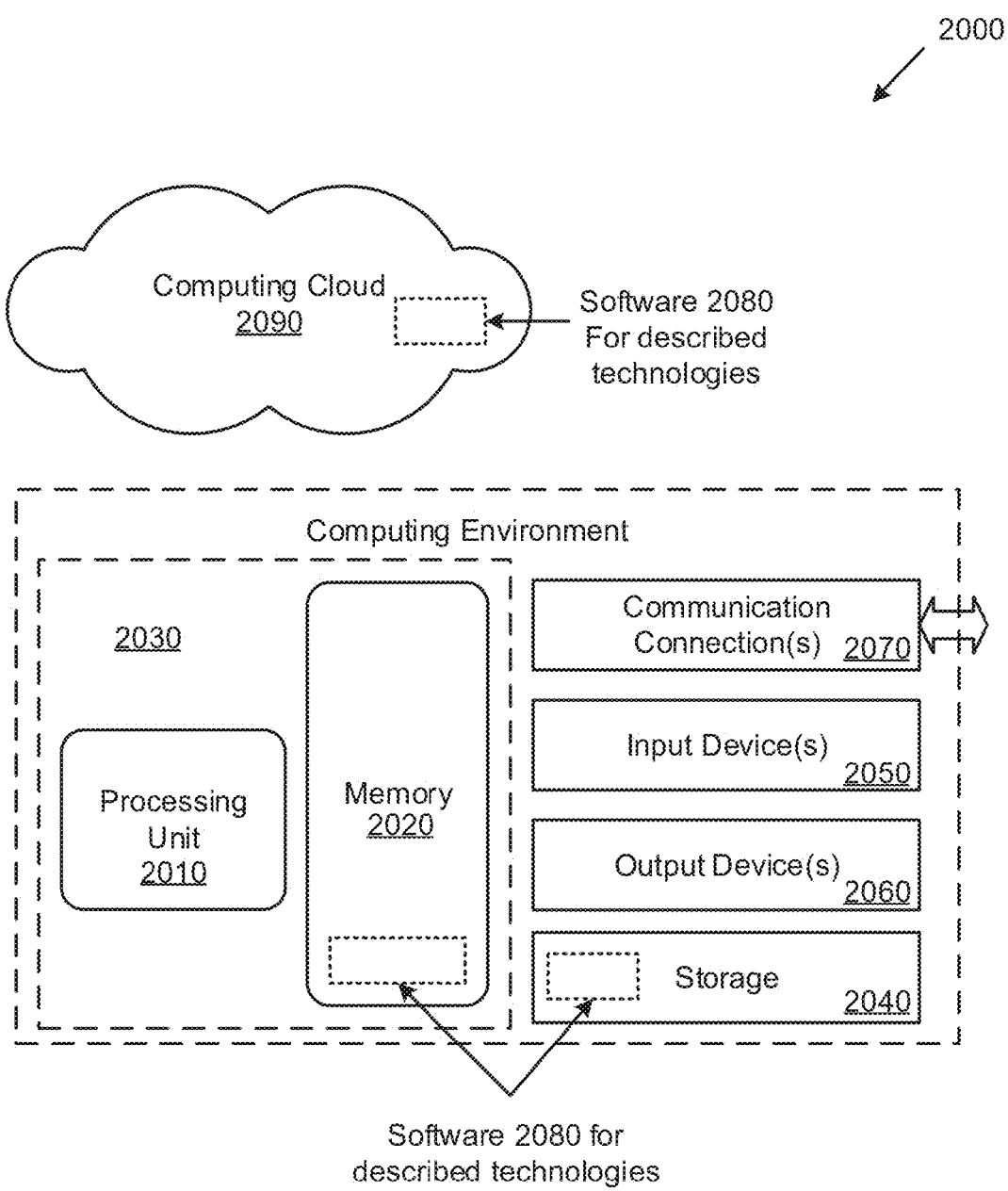
FIG. 21 illustrates a generalized example of a suitable computing environment in which described embodiments, techniques, and technologies can be implemented.

FIG. 21 illustrates a generalized example of a suitable computing environment 2000 in which described embodiments, techniques, and technologies can be implemented. For example, the computing environment 2000 can be used to receive intensity data, apply invertible matrix transforms, and filter transformed data, as described above.

The computing environment 2000 is not intended to suggest any limitation as to scope of use or functionality of the technology, as the technology can be implemented in diverse general-purpose or special-purpose computing environments. For example, the disclosed technology can be implemented with other computer system configurations, including hand held devices, multiprocessor systems, microprocessor-based or programmable consumer electronics, network PCs, minicomputers, mainframe computers, and the like. The disclosed technology can also be practiced in distributed computing environments where tasks are performed by remote processing devices that are linked through a communications network. In a distributed computing environment, program modules can be located in both local and remote memory storage devices.

With reference to FIG. 21, the computing environment 2000 includes at least one central processing unit 2010 and memory 2020. In FIG. 21, this most basic configuration 2030 is included within a dashed line. The central processing unit 2010 executes computer-executable instructions and can be a real or a virtual processor. In a multi-processing system, multiple processing units execute computer-executable instructions to increase processing power and as such, multiple processors can be running simultaneously. In some examples, FPGAs or other reconfigurable logic devices can be used to augment, or instead of, the central processing unit 2010 and/or memory 2020. The memory 2020 can be volatile memory (e.g., registers, cache, RAM), non-volatile memory (e.g., ROM, EEPROM, flash memory, etc.), or some combination of the two. The memory 2020 stores software 2080 that can, for example, implement the technologies described herein. A computing environment can have additional features. For example, the computing environment 2000 includes storage 2040, one or more input devices 2050, one or more output devices 2060, and one or more communication connections 2070. An interconnection mechanism (not shown) such as a bus, a controller, or a network, interconnects the components of the computing environment 2000. Typically, operating system software (not shown) provides an operating environment for other software executing in the computing environment 2000, and coordinates activities of the components of the computing environment 2000.

The storage 2040 can be removable or non-removable, and includes magnetic disks, magnetic tapes or cassettes, CD-ROMs, CD-RWs, DVDs, or any other medium which can be used to store information and that can be accessed within the computing environment 2000. The storage 2040 stores instructions for the software 2080 and data (e.g., measurement data or correlation data), which can be used to implement technologies described herein.

The input device(s) 2050 can be a touch input device, such as a keyboard, keypad, mouse, touch screen display, pen, or trackball, a voice input device, a scanning device, or another device, that provides input to the computing environment 2000. For audio, the input device(s) 2050 can be a sound card or similar device that accepts audio input in analog or digital form, or a CD-ROM reader that provides audio samples to the computing environment 2000. The output device(s) 2060 can be a display, printer, speaker, CD-writer, or another device that provides output from the computing environment 2000.

The communication connection(s) 2070 enable communication over a communication medium (e.g., a connecting network) to another computing entity. The communication medium conveys information such as computer-executable instructions, compressed graphics information, video, or other data in a modulated data signal.

The input device(s) 2050, output device(s) 2060, and communication connection(s) 2070 can be used with a control system to control inputs and/or outputs for a spectrometer. For example, input devices can be used with a control system for modulating an ESI transmitter, an ion gate, or gas inputs and outputs of a mass spectrometer. Further, output devices can be used with a control system for sampling or removing analytes or gases from a spectrometry system. In some examples, a communication connection 2070, such as an RS 232, USB, Ethernet, or other suitable connection, is used to control spectrometer operation and detection.

Some embodiments of the disclosed methods can be performed using computer-executable instructions implementing all or a portion of the disclosed technology in a computing cloud 2090. For example, applying Hadamard transforms and filtering data by removing symmetric pairs can be performed on servers located in the computing cloud 2090.

Computer-readable media are any available media that can be accessed within a computing environment 2000 and include, by way of example, and not limitation, include memory 2020 and/or storage 2040. As should be readily understood, the term computer-readable storage media includes the media for data storage such as memory 2020 and storage 2040, and not transmission media carrying modulated data signals or transitory signals.

Any of the methods described herein can be performed via one or more computer-readable media (e.g., storage or other tangible media) comprising (e.g., having or storing) computer-executable instructions for performing (e.g., causing a computing device to perform) such methods. Operation can be fully automatic, semi-automatic, or involve manual intervention.

Having described and illustrated the principles of our innovations in the detailed description and accompanying drawings, it will be recognized that the various embodiments can be modified in arrangement and detail without departing from such principles. It should be understood that the programs, processes, or methods described herein are not related or limited to any particular type of computing environment, unless indicated otherwise. Various types of general purpose or specialized computing environments can be used with or perform operations in accordance with the teachings described herein. Elements of embodiments shown in software can be implemented in hardware and vice versa.

In view of the many possible embodiments to which the principles of the disclosed invention may be applied, it should be recognized that the illustrated embodiments and their equivalents are only preferred examples of the invention and should not be taken as limiting the scope of the invention.

We claim:

1. A method of analyzing a sample containing a plurality of analytes, comprising:
   introducing two or more ion packets comprising accumulated ions from the multiple analytes in the sample in succession from an ion funnel into a drift region of an ion mobility separation stage at time intervals that are other than constant and encoded by a first pulse sequence;
   separating ions in the two or more ion packets in the drift region of the ion mobility separation stage at each of the time intervals to obtain separation profiles therefore;
   releasing ions in the two or more separated ion packets with control circuitry from the drift region of the mobility separation stage through an ion gate into an ion trap mass spectrometer at time intervals encoded by a second pulse sequence, wherein the release of ions into the ion trap mass spectrometer is performed with a double multiplexing from which double multiplexed data is created;

shifting the double multiplexed data by a pre-determined scan number to reduce artifacts in the double multiplexed data;

recovering single multiplexed data from the double multiplexed data;

decoding the single multiplexed data to produce decoded data;

shifting the decoded data back by the pre-determined scan number to preserve accurate arrival times; and determining a species of the ions based on the decoded data.

2. The method of claim 1, wherein the act of recovering comprises a least squares projection technique, and a first basis space of the double multiplexed data is projected onto a second basis space of single multiplexed data.

3. The method of claim 1, wherein the act of decoding comprises using an inverse simplex matrix.

4. The method of claim 1, wherein the mass spectrometer is an ion trap mass spectrometer.

5. The method of claim 4, wherein the mass spectrometer is an Orbitrap mass spectrometer.

6. The method of claim 1, wherein the act of recovering comprises multiplying the double multiplexing data by an inverse matrix.

7. The method of claim 1, wherein shifting the decoded data back by the pre-determined scan number maximizes an intensity of the decoded data.

8. The method of claim 1, wherein the number of ion releases through the ion gate is defined by a binary term $2^N-1$ in the second pulse sequence where N is the number of data bits in the second pulse sequence.

9. The method of claim 1, wherein the first pulse sequence is the same as the second pulse sequence.

10. The method of claim 1, wherein the first pulse sequence is different than the second pulse sequence.

11. The method of claim 1, wherein a length of the first pulse sequence is the same as a length of the second pulse sequence.

12. The method of claim 1, wherein a length of the first pulse sequence is different than a length of the second pulse sequence.

13. The method of claim 1, wherein 4-bit multiplexing is used to generate the double multiplexed data.

14. The method of claim 13, wherein the double multiplexed data includes 29 elements.

15. The method of claim 14, wherein the 29 elements includes 23 peaks.

16. A method of analyzing a sample containing a plurality of analytes, comprising:

receiving double multiplexed data from a device, wherein the device comprises:

an ion mobility separation stage with a drift region therein coupled to an ion trap mass spectrometer, wherein the separation stage is configured to receive two or more ion packets comprising ions from multiple analytes in a sample in succession from an ion funnel trap at time intervals that are other than constant encoded by a first pulse sequence that separates the ions in the drift region therein;

an ion gate disposed at an end of the drift region in front of the ion trap mass spectrometer; and control circuitry configured to release ions in two or more separated ion packets from the drift region through the ion gate into the ion trap mass spectrometer at time intervals encoded by a second pulse sequence within the acquisition time of the ion trap mass spectrometer;

recovering single multiplexed data from the double multiplexed data, which comprises:

generating a first matrix S that includes the single multiplexed data;

generating a second matrix A that includes the double multiplexed data;

resizing the second matrix A to a third matrix R;

generating a fourth matrix $S^T$, wherein $S^T$ is a transpose matrix of the first matrix S;

calculating $(S^T \times S)^{-1} \times S^T \times R$ to generate a fifth matrix; and shifting the double multiplexed data by a scan number to reduce artifacts in the double multiplexed data;

decoding the single multiplexed data, thereby producing decoded data;

shifting the decoded data back by the scan number to preserve accurate arrival times; and determining a species of the ions based on the decoded data.

17. The method of claim 16, wherein the first matrix S comprises a size n×m and is generated from an encoding pseudo-random sequence, and wherein n is a length of the pseudo-random sequence and m=2*n−1.

18. The method of claim 17, wherein the first matrix S is a block diagonal matrix, and each diagonal block contains a reverse pseudo-random sequence.

19. The method of claim 18, wherein the second matrix A is a size k×l, and where k is a m/z dimension and l is a drift time dimension in scan numbers.

20. The method of claim 19, wherein the double multiplexed date is shifted by a maximum intensity scan number.

21. The method of claim 20, wherein the double multiplexed data is encoded by a pseudo-random sequence and an oversampling number which determines a number of segments per row, the number of segments is obtained by dividing a row count by a length of the oversampling number, and the third matrix R has a row count equal to the number of segments and a column count equal to the oversampling number.

22. The method of claim 21, further comprising resizing the fifth matrix to the row size of the second matrix A.

23. The method of claim 22, further comprising validating the product of the calculation.

24. A system, comprising:

an ion mobility separation stage with a drift region therein coupled to an ion trap mass spectrometer, wherein the separation stage is configured to receive two or more ion packets comprising ions from multiple analytes in a sample in succession from an ion funnel trap at time intervals that are other than constant encoded by a first pulse sequence that separates the ions in the drift region therein;

an ion gate disposed at an end of the drift region in front of the ion trap mass spectrometer;

control circuitry; and a computing device comprising instructions for controlling the control circuitry, wherein the control circuitry is configured to release ions in two or more separated ion packets from the drift region through the ion gate into the ion trap mass spectrometer at time intervals encoded by a second pulse sequence within the acquisition time of the ion trap mass spectrometer, wherein the control circuitry is configured to the release of ions into the ion trap mass spectrometer with double multiplexing from which double multiplexed data is generated, wherein computing device further includes instructions for:

decoding the double multiplexed data by projecting the double multiplexed data directly onto a basis space of a decoded signal and by transforming an inverse transform matrix by pre-multiplying the inverse transform matrix with an inverse simplex matrix;

shifting the double multiplexed data by a pre-determined scan number to reduce artifacts in the double multiplexed data; and shifting the decoded data back by the pre-determined scan number to preserve accurate arrival times.

25. The system of claim 24, wherein the second pulse sequence includes a binary term $2^N-1$ that defines the number of ion releases through the ion gate where N is the number of data bits in the second pulse sequence.

26. A system of claim 24, wherein the first pulse sequence of the ion mobility separation stage is the same as or different than the second pulse sequence of the ion trap mass spectrometer.

27. A system of claim 24, wherein a length of the first pulse sequence of the ion mobility separation stage is the same as or different than a length of the second pulse sequence of the ion trap mass spectrometer.

28. The system of claim 24, wherein the ion trap mass spectrometer is an Orbitrap mass spectrometer.

* * * * *